United States Patent
Lemke et al.

(12) 
(10) Patent No.: US 7,875,037 B2
(45) Date of Patent: Jan. 25, 2011

(54) INFANT UMBILICAL CORD CARDIAC MONITORING SYSTEM AND METHOD

(75) Inventors: Robert Lemke, Sherwood Park (CA); Mike Farrah, Spruce Grove (CA); Paul Byrne, Edmonton (CA)

(73) Assignee: Jengstar-MD Medical Technologies Ltd., Sherwood Park (CA)

( * ) Notice: Subject to any disclaimer, the term of this patent is extended or adjusted under 35 U.S.C. 154(b) by 738 days.

(21) Appl. No.: 11/878,201

(22) Filed: Jul. 23, 2007

(65) Prior Publication Data

US 2009/0030318 A1    Jan. 29, 2009

(51) Int. Cl.
  *A61B 17/42* (2006.01)
  *A61B 5/00* (2006.01)
  *A61B 8/14* (2006.01)

(52) U.S. Cl. .................. 606/120; 600/301; 600/459

(58) Field of Classification Search ............... 600/301, 600/304, 407, 438, 454, 459, 504; 606/119, 606/120
See application file for complete search history.

(56) References Cited

U.S. PATENT DOCUMENTS

| | | | |
|---|---|---|---|
| 5,415,665 A * | 5/1995 | Hessel et al. | 606/120 |
| 5,749,831 A | 5/1998 | Baker | |
| 7,291,109 B1 * | 11/2007 | Sarvazyan | 600/438 |

* cited by examiner

*Primary Examiner*—Long V Le
*Assistant Examiner*—Michael T Rozanski
(74) *Attorney, Agent, or Firm*—Macleod Dixon LLP

(57) ABSTRACT

An infant umbilical cord monitoring system having a hinged housing adapted to receive both an umbilical cord clamping means and a means for measuring physiological data of the infant. A method of using an infant's umbilical cord for obtaining physiological data includes applying an umbilical cord clamping means to the infant's umbilical cord, positioning a hinged housing adapted to receive both the umbilical cord clamping means and a means for measuring physiological data of the infant against the infant and detecting the physiological data of the infant.

20 Claims, 4 Drawing Sheets

INFANT UMBILICAL CORD CARDIAC MONITORING SYSTEM AND METHOD

FIELD OF THE INVENTION

This invention relates in general to an infant monitoring device and more particularly to a device and method for monitoring an infant's physiological information using the infant's umbilical cord.

BACKGROUND OF THE INVENTION

The transition from a fetus to an air breathing infant is a complex process that in general is successfully accomplished. However a significant number of births often require some type emergent assistance or intervention during this transition. The type of assistance or intervention can vary depending on the situation. Simple stimulation, cardiopulmonary resuscitation or the administration of powerful cardiac drugs such as adrenalin may be needed by way of example.

To determine whether the newborn infant requires resuscitative assistance, the resuscitation team must be able to obtain real time knowledge of a baby's rapidly changing heart rate. Currently physicians and support staff are able to accurately determine the heart rate of fetuses in the womb, and older infants. For example, U.S. Pat. No. 5,749,831 issued on May 12, 1998 to Baker relates to methods and systems for monitoring to assess the health of a fetus being carried within a mother. The methods include sensing fetal heart information using a fetal heart sensor; determining at least one fetal heart rate measure from the fetal heart rate information; detecting umbilical flow information relating to the flow of blood within the umbilical cord; deriving at least one umbilical flow indicator from at least the umbilical flow information; and analyzing the fetal heartbeat measure and umbilical flow measure to produce at least one fetal health parameter.

However with a newborn infant, and especially in a compromised newborn infant, the resuscitation team is limited specifically to physical examination via palpation and auscultation during the critical period of time between clamping of the umbilical cord and the application of electronic monitoring devices. It is well known that currently the quickest and most accurate method to determine a newborn infant's heart rate is to palpate the pulse at the base of the infant's umbilical cord. Alternatively the heart rate may be determined by using a stethoscope and listening to heart beat over the left side of the infant's chest. However the resulting palpation or auscultation derived heart rate measurements are subjectively determined and provide only intermittent information. Furthermore this task is frequently done under very stressful circumstances and is therefore intrinsically prone to error which is magnified when the task is conducted by inexperienced individuals.

The result is that some infants who do not warrant intervention may undergo invasive and potentially deleterious interventions including intubation (i.e. placement of a breathing tube), artificial ventilation and even external cardiac message. Conversely other patients who desperately need these types procedures may not receive them and therefore remain compromised for critical minutes until the resuscitators recognize that the infant is not improving with simple stimulation and oxygen administration.

Prior art devices have tried to provide electronic monitoring in the delivery suite to neonates immediately after delivery. These devices have unfortunately met with limited success. Their limited success is in part due to the blood, mucus, amniotic fluid and vernix caseosa that covers the infant at birth. This must be cleaned from the skin to ensure that any adhesive probes are attached properly and that there is good skin to probe contact allowing for accurate readings. Secondly, some monitoring devices, notably pulse oximetry, depend on good tissue perfusion to ensure an error free signal. Unfortunately, those infants who are in the most serious trouble have the most compromised skin perfusion, so accurate readings are difficult to obtain. Finally in all cases there is a time delay between the moment the umbilical cord is cut, to when the monitors are applied to the infant during which physiological data can not be collected.

Thus an infant umbilical cord monitoring system which is easy and fast to apply to an infant and provides immediate physiological data about the infant is desirable.

SUMMARY OF THE INVENTION

An object of one aspect of the present invention is to provide an optimal infant monitoring system using a newborn infant's umbilical cord as an attachment point allowing for the measurement of the infant's physiological data either from the umbilical cord itself or from structures in the infant's abdomen such as the abdominal aorta, that are adjacent to the umbilical cord.

In accordance with one aspect of the present invention there is provided an infant umbilical cord monitoring system having a hinged housing designed to receive both a specific umbilical cord clamping means and a means for measuring physiological data either from the umbilical cord itself or from structures in the infant's abdomen such as the abdominal aorta, that are adjacent to the umbilical cord.

Conveniently, the hinged housing further includes a first end and a second end and an orifice that extends from the first end to the second end and adapted to receive the infant umbilical cord.

Preferably the hinged housing further includes a slot adapted to receive the umbilical cord clamping means and an orifice adapted to receive the means for measuring the physiological data.

In accordance with another aspect of the invention there is provided a method of using an infant's umbilical cord as an attachment point for obtaining physiological data. The method includes applying an umbilical cord clamping means to the infant's umbilical cord, positioning a hinged housing adapted to receive both the umbilical cord clamping means and a means for measuring physiological data of the infant against the infant and detecting the physiological data either from the umbilical cord itself or from structures in the infant's abdomen such as the abdominal aorta, that are adjacent to the umbilical cord.

Advantages of the present invention are: the monitoring system is up and functioning as soon as possible after delivery of the infant thereby providing immediate data, the monitoring system is fast and easy to attach to the infant, provides accurate data under conditions of severe cardio respiratory compromise or shock for example, and provides continuous, real time heart rate measurement.

BRIEF DESCRIPTION OF THE DRAWINGS

A detailed description of the preferred embodiments is provided herein below by way of example only and with reference to the following drawings, in which.

Figure 1A:
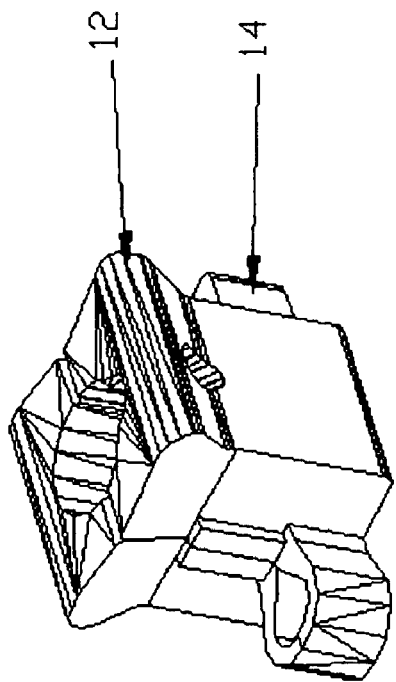
FIG. 1a in a perspective view, illustrates an infant umbilical cord monitoring system in accordance with a preferred embodiment of the present invention.

In the drawings, preferred embodiments of the invention are illustrated by way of example only. It is to be expressly understood that the description and drawings are only for the purpose of illustration and as an aid to understanding, and are not intended as a definition of the limits of the invention.

DETAILED DESCRIPTION OF THE PREFERRED EMBODIMENT

Figure 1B:
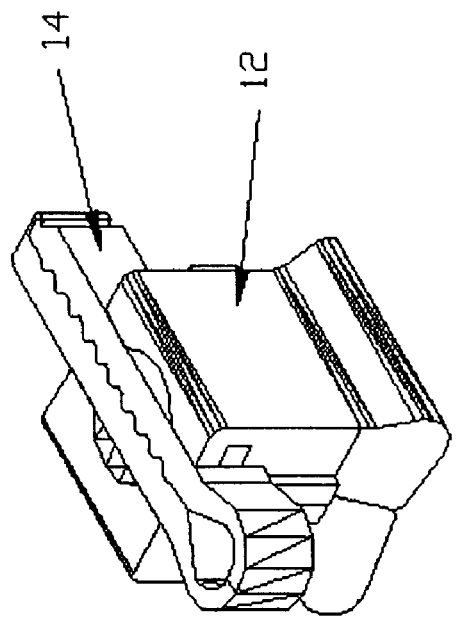
FIG. 1b in a perspective view, illustrates an infant umbilical cord monitoring system in accordance with a preferred embodiment of the present invention.
Figure 1C:
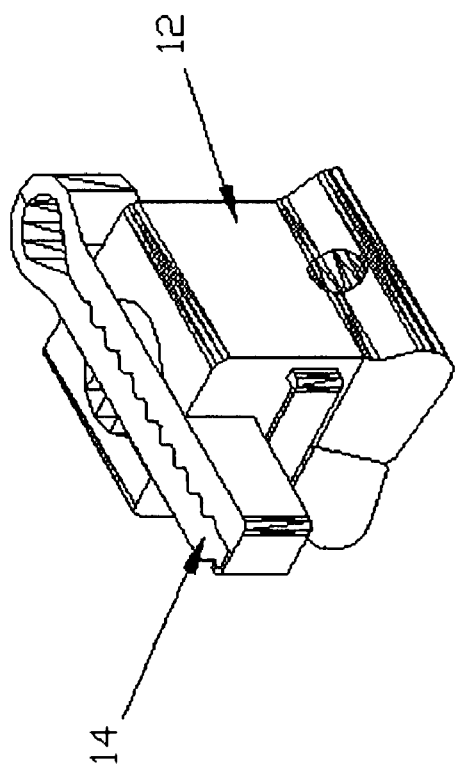
FIG. 1c in a perspective view, illustrates an infant umbilical cord monitoring system in accordance with a preferred embodiment of the present invention.
Figure 1D:
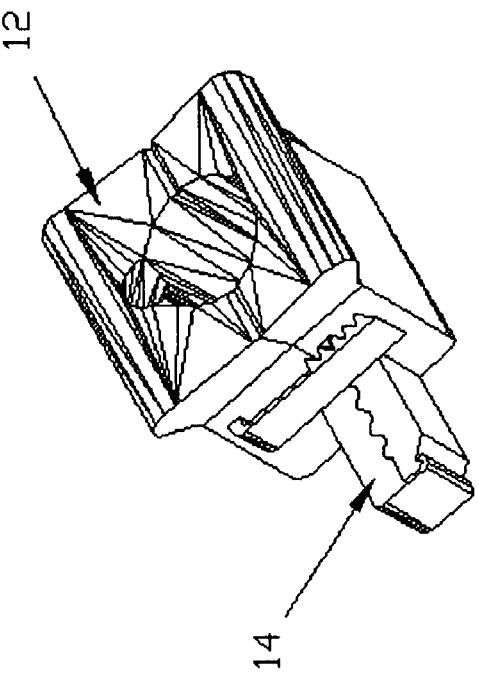
FIG. 1d in a perspective view, illustrates an infant umbilical cord monitoring system in accordance with a preferred embodiment of the present invention.
Figure 2C:
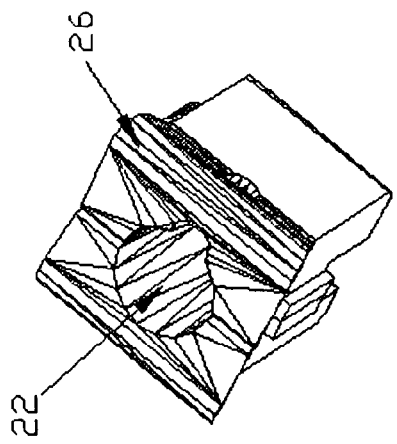
FIG. 2c in a perspective view, illustrates the hinged housing of the infant umbilical cord monitoring system of FIG. 1.
Figure 2B:
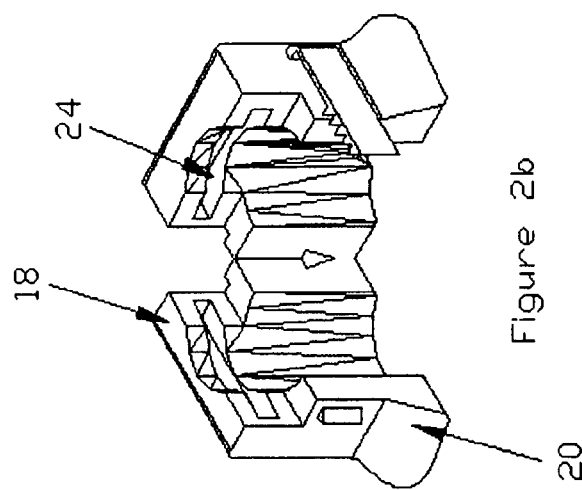
FIG. 2b in a perspective view, illustrates the hinged housing of the infant umbilical cord monitoring system of FIG. 1.
Figure 2E:
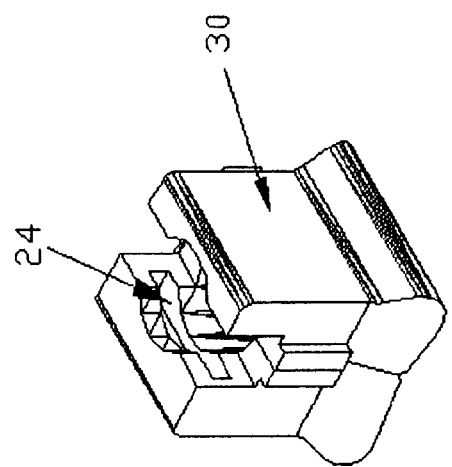
FIG. 2e in a perspective view, illustrates the hinged housing of the infant umbilical cord monitoring system of FIG. 1.
Figure 2A:
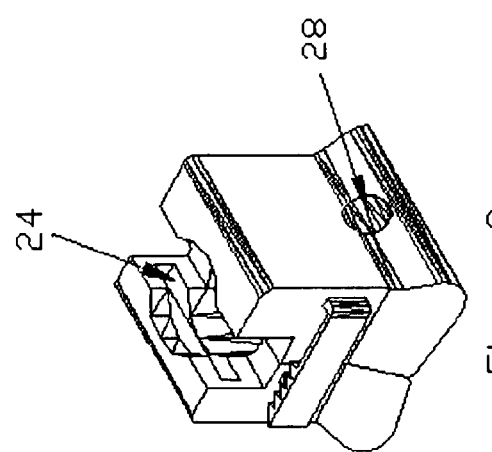
FIG. 2a in a perspective view, illustrates a hinged housing of the infant umbilical cord monitoring system of FIG. 1.
Figure 2D:
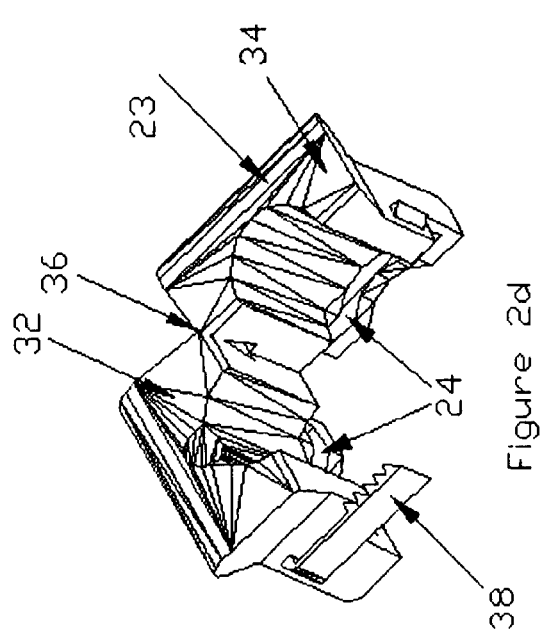
FIG. 2d in a perspective view, illustrates the hinged housing of the infant umbilical cord monitoring system of FIG. 1.
Figure 3A:
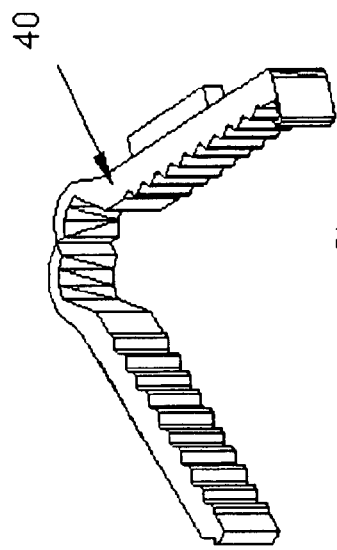
FIG. 3a in a perspective view, illustrates an umbilical cord clamping means of the infant umbilical cord monitoring system of FIG. 1.
Figure 3B:
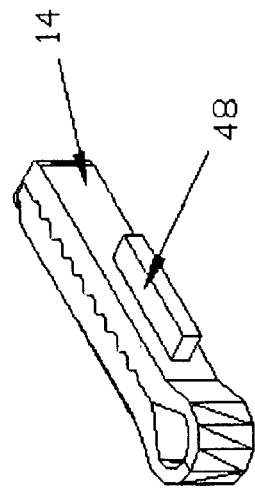
FIG. 3b in a perspective view, illustrates the umbilical cord clamping means of the infant umbilical cord monitoring system of FIG. 1.
Figure 3C:
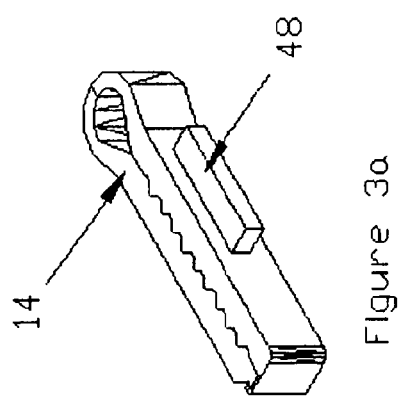
FIG. 3c in a perspective view, illustrates the umbilical cord clamping means of the infant umbilical cord monitoring system of FIG. 1.
Figure 3D:
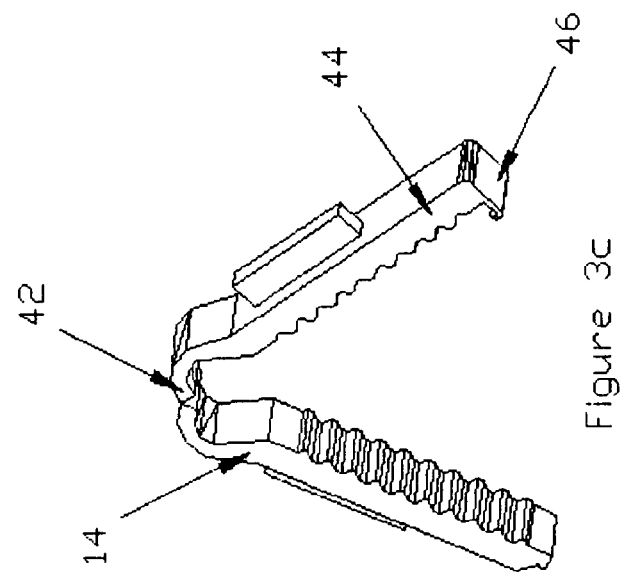
FIG. 3d in a perspective view, illustrates the umbilical cord clamping means of the infant umbilical cord monitoring system of FIG. 1.
Figure 4:
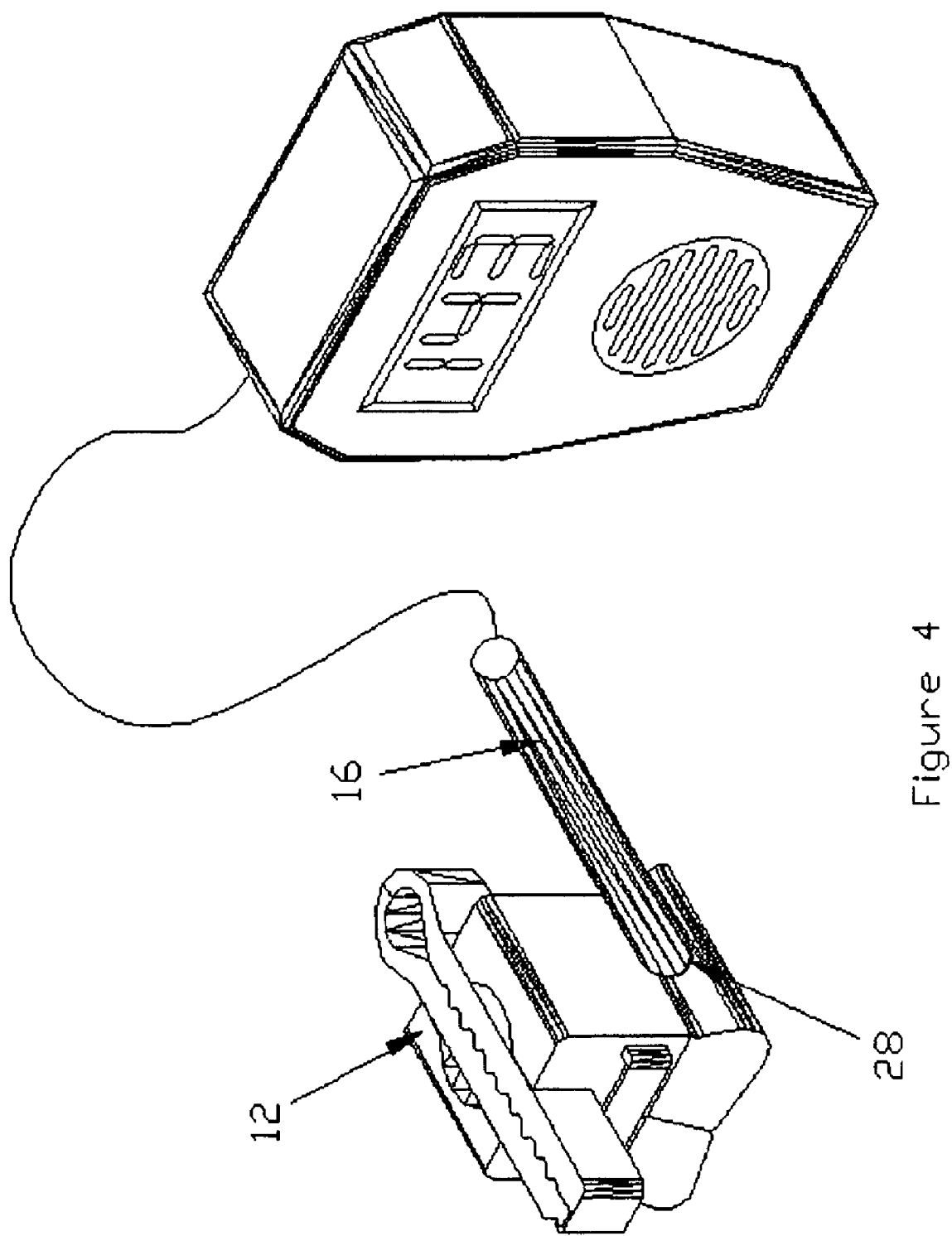
FIG. 4 in a perspective view, illustrates the assembled infant umbilical cord monitoring system of FIG. 1.

Referring to FIGS. 1 to 4, there is illustrated in perspective views, an infant umbilical cord monitoring system 10 in accordance with a preferred embodiment of the present invention. The infant umbilical cord monitoring system 10 includes a hinged housing 12 adapted to receive both an umbilical cord clamping means 14 and a means for measuring physiological data 16 either from the umbilical cord itself or from structures in the infant's abdomen such as the abdominal aorta, that are adjacent to the umbilical cord.

The hinged housing 12 further includes a first end 18 and a second end 20 and an orifice 22 that extends from the first end 18 to the second end 20 and is adapted to receive the infant umbilical cord. The orifice 22 may have a textured surface surrounding it 23 so as to provide traction against the infant umbilical cord when in use.

The hinged housing 12 may be further defined as a clamp 30 having a first portion 32 and a second portion 34. The first portion 32 and second portion 34 may move between an open position and a closed position. The first portion 32 and the second portion 34 are joined together by a hinge 36 allowing the hinged housing 12 to act as a clamp 30. The first and second portions 32 and 34 may be secured together by a locking mechanism 38 that secures the infant umbilical cord monitoring system 10 in the closed position. The locking mechanism 38 may be a ribbed bar with corresponding latch by way of example.

The first end 18 of the hinged housing 12 further includes at least one slot 24 that is adapted to receive the umbilical cord clamping means 14. The second end 20 of the hinged housing 12 has a surface 26 adapted to engage the infant. The first end 18 of the hinged housing 12 can further include an orifice 28 that is adapted to receive the means for measuring the physiological data 16.

The umbilical cord clamping means 14 may be further defined as a clamp 40 having a hinged first end 42 and a second end 44 having a locking mechanism 46. The lock mechanism 46 may be a simple latch by way of example. The clamp 40 may further include two slot members 48 adapted to engage the slot 24 in the hinged housing 12 to secure the clamp 40 to the hinged housing 12. The clamp 40 may have two slot members 48. The hinged housing 12 adapted to receive the umbilical cord clamping means 14 may be made from sterile, disposable, plastic by way of example. Furthermore once the infant has been resuscitated and the relevant physiological data collected, the hinged housing 12 may be removed as it is no longer needed and the umbilical cord clamping means 14 can remain without having to change to an alternate umbilical cord clamp to ensure homeostasis from the infant's umbilical cord.

The means for measuring physiological data 16 of the infant may be further defined as an ultrasound unit able to measure the physiological data of the infant via pulsations from large blood vessels either in the abdomen or in the infant's umbilical cord. The orifice 28 adapted to receive the means for measuring physiological data 16 of the infant may be positioned in the hinged housing 12 at a 45° angle to the infant by way of example. Other means for measuring physiological data 16 include electric (detection of electrical signals generated by the heart as typically used to generate a EKG), mechanical (detection of pulsation in the cord via a pressure transducer) or a combination of the two to provide similar if not identical physiological information.

In accordance with another preferred embodiment of the invention there is provided a method of obtaining physiological data using an infant's umbilical cord or from structures in the infant's abdomen, such as the abdominal aorta, that are adjacent to the umbilical cord. The method includes applying an umbilical cord clamping means 14 to the infant's umbilical cord, positioning a hinged housing 12 adapted to receive both the umbilical cord clamping means 14 and a means for measuring physiological data 16 of the infant against the infant and detecting the physiological data either from the umbilical cord itself or from structures in the infant's abdomen such as the abdominal aorta, that are adjacent to the umbilical cord. Mild tension may be applied to the umbilical cord when the infant umbilical cord monitoring system 10 is applied to the umbilical cord to ensure the infant umbilical cord monitoring system 10 is securely engaging the infant's abdominal skin.

In operation the infant umbilical cord monitoring system 10 is first utilized in the delivery suite. Typically once an infant is born, the physician or midwife applies a commercially available, sterile, disposable, cord clamp 1 to 3 cm above the baby's skin, applies a surgical hemostat above the cord clamp and then cuts between the two of them. The infant is then handed off to the resuscitation team for assessment. In the instant invention the infant umbilical cord monitoring system 10 simply replaces the current cord clamp. Specifically the infant's umbilical cord passes through the orifice 22 of the hinged housing 12 from the second end 20 to the first end 18, so that the surface 26 of the second end 20 of the hinged housing 12 is positioned next to the skin of the infant at the base of the umbilical cord. The slot members 48 of the umbilical cord clamping means 14 engage the slots 24 of the hinged housing 12.

The means for measuring physiological data 16, an ultrasound probe, by way of example, is then inserted into the orifice 28 of the hinged housing 12. By way of example only, the hinged housing 12 may hold an 8 to 9 MHz ultrasound probe at 45° to the infant's skin surface so as to detect the pulsations of the abdominal aorta. The ultrasound probe's signal is then analyzed electronically to determine heart rate in real time, which is then displayed numerically. A physical requirement is that the hinged housing 12 sit next to the infant's skin at the base of the umbilical cord and that there is mild traction of the umbilical cord through the hinged housing 12 to ensure that the infant umbilical cord monitoring system 10 does not "flop" around.

The infant umbilical cord monitoring system 10 allows for accurate real time heart rate measurement under a range of difficult conditions including severe cardio respiratory compromise or shock. The accuracy of the measurement is partially achieved by using a means for measuring physiological data 16 that is unaffected by the contamination of the skin with bodily fluids, ultrasound for example. This is achieved by employing the umbilical cord clamping means 14 and the hinged housing 12 to utilize the infant's umbilical cord to obtain the physiological data either from the umbilical cord itself or from structures in the infant's abdomen that are adjacent to the umbilical cord. The data can be efficiently collected even in difficult environments namely a newborn infant that is covered in mucus and fluid.

Furthermore the infant umbilical cord monitoring system 10 allows for the collection of the data in an easy, quick and accurate manner by way of its attachment to the infant's umbilical cord and by obtaining physiological data either from the umbilical cord itself or from structures in the infant's abdomen, such as the abdominal aorta, that are adjacent to the umbilical cord.

The instant method utilizes the infant's umbilical cord so as to measure the pulsation of the aorta in the abdomen, which is still present even under conditions of profound compromise in an infant. Furthermore the measurement of physiological data can be accurately obtained with the current method irregardless of the level of skin perfusion in the infant.

The use of the umbilical cord as a vehicle to accurately determine the physiological data allows for this data to be quickly accessed as the initial intervention in any infant immediately after delivery is to clamp and cut the umbilical cord. The clamping of the infant's umbilical cord provides a robust mechanical method of fixation for the infant umbilical cord monitoring system 10 which is unaffected by the presence of bodily fluids.

Furthermore the use of the umbilical cord is an ideal site for the infant umbilical cord monitoring system 10 as it is central on the body, universally present, contains no pain receptors and is not needed after birth. Moreover the application of the infant umbilical cord monitoring system 10 at the time the cord is clamped also functions as, and has integral to it, the umbilical cord clamping means 14 which can continue to be used once the hinged housing 12 is removed. The infant umbilical cord monitoring system 10 therefore is functioning at the first possible moment after the delivery of the infant and physiological data, namely heart rate data, can therefore be obtained before the infant is even transferred to and assessed by the resuscitation team. The infant umbilical cord monitoring system 10 therefore gives the ability to immediately monitor a critically ill infant almost immediately after birth and for the hours after birth which may be most beneficial in locations that have limited experience with critically ill newborns.

Other variations and modifications of the invention are possible. All such modifications or variations are believed to be within the sphere and scope of the invention as defined by the claims appended hereto.

We claim:

1. An infant umbilical cord monitoring system utilized at birth comprising:
   a hinged housing having a central opening configured to surround an umbilical cord, the hinged housing having a first side and a second side opposite to the first side that is configured to contact the infant, the first side of the hinged housing is adapted to receive an umbilical cord clamping means such that the umbilical cord clamping means is configured to engage the umbilical cord as the umbilical cord passes through the central opening, and a means for measuring immediately and in real time physiological data of the infant continuously from the moment of birth which passes through an orifice on another side of the hinged housing wherein the means for measuring immediately and in real time physiological data is configured to be in direct contact with the infant and/or the infant's umbilical cord.

2. An infant umbilical cord monitoring system as claimed in claim 1 wherein the first side of the hinged housing further comprises at least one slot adapted to receive the umbilical cord clamping means.

3. An infant umbilical cord monitoring system as claimed in claim 2 wherein the umbilical cord clamping means is a clamp having a hinged first end and a second end having a locking mechanism.

4. An infant umbilical cord monitoring system as claimed in claim 3 wherein the clamp further comprises at least one slot member adapted to engage the slot in the hinged housing to secure the clamp to the hinged housing.

5. An infant umbilical cord monitoring system as claimed in claim 1 wherein the hinged housing is a clamp having a first portion and a second portion able to move between an open position and a closed position.

6. An infant umbilical cord monitoring system as claimed in claim 5 wherein the first portion and the second portion are joined together by a hinge.

7. An infant umbilical cord monitoring system as claimed in claim 5 wherein the first and second portions are secured together by a locking mechanism.

8. An infant umbilical cord monitoring system as claimed in claim 5 wherein the orifice is positioned in the hinged housing at an angle and is adapted to receive the means for measuring physiological data of the infant.

9. An infant umbilical cord monitoring system as claimed in claim 1 wherein the central opening has a textured surface configured to provide traction against the infant umbilical cord.

10. An infant umbilical cord monitoring system as claimed in claim 1 wherein the means for measuring physiological data of the infant is an ultrasound unit.

11. An infant umbilical cord monitoring system as claimed in claim 1 wherein the means for measuring physiological data of the infant is an electric device, a mechanical device or an electrical/mechanical device.

12. An infant umbilical cord monitoring system as claimed in claim 11 wherein the electrical device is an electrocardiogram.

13. An infant umbilical cord monitoring system as claimed in claim 11 wherein the mechanical device is a pressure transducer.

14. An infant umbilical cord monitoring system as claimed in claim 11 further comprising a device that measures arterial pulsations that are intra-abdominal at a distance from the umbilical cord.

15. An infant umbilical cord monitoring system as claimed in claim 1 wherein the infant umbilical cord monitoring system is disposable.

16. A method of obtaining physiological data at birth using an infant's umbilical cord or from structures in the infant's abdomen that are adjacent to the umbilical cord comprising:
  (a) applying an umbilical cord clamping means to the infant's umbilical cord;
  (b) positioning against the infant a hinged housing having a central opening configured to surround the umbilical cord, the hinged housing having a first side and a second side opposite to the first side that contacts the infant, the first side of the hinged housing is adapted to receive the umbilical cord clamping means such that the umbilical cord clamping means engages the umbilical cord as the umbilical cord passes through the central opening, and a means for measuring immediately and in real time physiological data of the infant continuously from the moment of birth which passes through an orifice on another side of the hinged housing wherein the means for measuring immediately and in real time physiological data is in direct contact with the infant and/or the infant's umbilical cord;
  (c) detecting the physiological data of the infant.

17. A method of obtaining physiological data using an infant's umbilical cord or from structures in the infant's abdomen that are adjacent to the umbilical cord as claimed in claim 16 wherein the means for measuring physiological data of the infant is by using ultrasound.

18. A method of obtaining physiological data using an infant's umbilical cord or from structures in the infant's abdomen that are adjacent to the umbilical cord as claimed in claim 16 wherein the means for measuring physiological data of the infant is by using an electric device, a mechanical device or an electrical/mechanical device.

19. A method of obtaining physiological data using an infant's umbilical cord or from structures in the infant's abdomen that are adjacent to the umbilical cord as claimed in claim 16 further comprising applying mild tension to the umbilical cord when positioning the umbilical cord within the hinged housing.

20. A method of obtaining physiological data using an infant's umbilical cord or from structures in the infant's abdomen that are adjacent to the umbilical cord as claimed in claim 16 further comprising detecting pulsation of the abdominal aorta in the infant.

* * * * *